United States Patent
Momoi et al.

(10) Patent No.: US 8,092,471 B2
(45) Date of Patent: Jan. 10, 2012

(54) POSITION MEASURING APPARATUS

(75) Inventors: Yasuyuki Momoi, Ushiku (JP); Madoka Sugiura, Yokohama (JP); Takahiro Ochi, Yokohama (JP); Kazuo Yonenobu, Ashiya (JP); Nobuhiko Sugano, Suita (JP); Yoshinobu Sato, Suita (JP); Yoshikazu Nakajima, Ibaraki (JP); Toshihiko Sasama, Tottori (JP); Takeyoshi Dohi, Tokyo (JP); Ichiro Sakuma, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 1320 days.

(21) Appl. No.: 10/716,485

(22) Filed: Nov. 20, 2003

(65) Prior Publication Data

US 2005/0015099 A1 Jan. 20, 2005

(30) Foreign Application Priority Data

Jul. 14, 2003 (JP) ................... 2003-196181

(51) Int. Cl.
*A61B 19/00* (2006.01)
(52) U.S. Cl. ........................ 606/130; 600/427
(58) Field of Classification Search .............. 606/129, 606/130; 600/411, 426, 427, 424, 429
See application file for complete search history.

(56) References Cited

U.S. PATENT DOCUMENTS

| | | | | |
|---|---|---|---|---|
| 5,662,111 A | * | 9/1997 | Cosman | 600/417 |
| 5,748,767 A | * | 5/1998 | Raab | 382/128 |
| 5,868,675 A | * | 2/1999 | Henrion et al. | 600/424 |
| 5,954,648 A | | 9/1999 | Van Der Brug | |
| 6,187,018 B1 | * | 2/2001 | Sanjay-Gopal et al. | 606/130 |
| 6,405,072 B1 | * | 6/2002 | Cosman | 600/426 |
| 6,447,503 B1 | | 9/2002 | Wynne et al. | |
| 7,305,319 B2 | * | 12/2007 | Vicci et al. | 702/152 |
| 2001/0034530 A1 | * | 10/2001 | Malackowski et al. | 606/130 |
| 2002/0188194 A1 | | 12/2002 | Cosman | |
| 2004/0085443 A1 | * | 5/2004 | Kallioniemi et al. | 348/135 |

FOREIGN PATENT DOCUMENTS

DE 100 377 771 A1 2/2002

OTHER PUBLICATIONS

"Development of the Laser Guidance System", Orthopedic Surgery of Osaka University, Japan, Feb. 18, 2003, and English Abstract thereof.
"Computer-Assisted Spinal Surgery Using Anatomy-Based Registration", by Stéphane Lavailée, et al., pp. 425-449, Orthopaedics.

(Continued)

*Primary Examiner* — Victor Nguyen
(74) *Attorney, Agent, or Firm* — Antonelli, Terry, Stout & Kraus, LLP.

(57) ABSTRACT

A position measuring apparatus, for use in an assisting apparatus for surgical opertions, includes a position indicating apparatus for indicating a position and a direction of a tool, and three-dimensional position measuring apparatus for measuring a position and a direction of a surgical field and also the position and the direction of the tool. The position indicating apparatus and the three dimensional position measuring apparatus are unified in one body in the relative position thereof, so that a position for assistance of surgical operation is indicated in the form of an intersection line or an intersection point of the laser beams, irrespective of the position of the position measuring apparatus.

14 Claims, 8 Drawing Sheets

OTHER PUBLICATIONS

"A Novel laser guidance system to present the information of navigation directly in the surgical field", by N. Sugano, et al., CAOS 2002 (The Second Annual Conference of the International Society for Computer Associated Orthopaedic Surgery) ('02.06.19).

"Computer Aided Pedicle Screw Placement Using a Novel Laser Guidance System", by Y. Tamura, et al, CAOS 2002 (The Second Annual Conference of the International Society for Computer Associated Orthopaedic Surgery) ('02.06.19).

"Clinical application of a laser guidance system with dual laser beam ryas as augumented reality of surgical navigation", by N. Nugano, et al, CARS 2002 (Computer Associated Radiology and Surgery, 16th International Congress and Exhibition) ('02.06.26).

"A Novel Laser Guidance System for Alignment of Linear Surgical Tools: Its Principles and Performance Evaluation as a Man-Machine System", by T. Sasama, et al., MICCAI 2002 ($5^{th}$ International Conference on Medical Image Computing and Computer-Assisted Intervention) ('02.09.25).

"Development of a Laser Guidance System using an Intersection line of Dual Laser Beam Plane", by Y. Momoi, et al., Conference of Japan Computer Surgery Association, Nov. 2002.

* cited by examiner

POSITION MEASURING APPARATUS

BACKGROUND OF THE INVENTION

The present invention relates to an assistance apparatus for a surgical operation, and in particular, it relates to a position measuring apparatus for it.

In a surgical operation, including an orthopedic operation, etc., for example, it is very important to conduct the positioning of a surgical tools or appliances, which is operated by a surgeon in the surgical operation, correctly. However, since it is difficult to conduct the positioning of such the surgical tools or appliances only depending upon visual information, which can be obtained by the surgeon from the portion where the surgical operation is done, then a research and/or study has been made on a use of navigation system, as an assistance of positioning of the surgical tools. Thus, in the INTERNET information mentioned below, there is proposed a laser pointing system, using a navigation system applying laser beams therein, wherein the surgeon can conduct the positioning of the surgical tool upon basis of track of the laser beams displayed thereon at hand, but without seeing a navigation display screen of the navigation system, thereby conducting the surgical operation, correctly.

Orthopedics, Osaka University, "Development of a Laser Guidance System", [online], [searched on Feb. 18, 2003], INTERNET <URL:http://www.med.osaka-u.ac.jp/pub/ort/www/hip/laser-point ing.html>

However, when conducting the surgical operation while indicating the position through the laser beam within a surgical field, sometimes the laser beam is obstructed or cutoff by a portion of a body of a patient or the surgical tools, etc., and in such the case, it is necessary to move the position of an outlet of the laser beam, so that the laser beam is not obstructed or cut off during the surgical operation. In this instance, a positional relationship is shifted between a position indicating means of emitting the laser beam and a position measuring means for measuring the position of the surgical field; i.e., the coordinates of both are shifted, therefore it is necessary to conduct a calibration operation for those coordinates of both to be coincide with each other. Also, when the outlets of the laser beams are moved accidentally or carelessly, it is necessary to conduct the calibration operation, in the similar manner. However, such the re-calibration operation during the surgical operation, it may results into a consumption of time.

BRIEF SUMMARY OF THE INVENTION

According to the present invention, being achieved by taking such the drawbacks of the conventional art mentioned above into the consideration, an object is to provide a position measuring apparatus, enabling to omit such the calibration operation after the movement of the position indicating means, in particular, in the navigation system, which can indicates a position and a direction of the tool.

For accomplishing the object as was mentioned in the above, according to the present invention, there is provided a position measuring apparatus, comprising: a position indicating means for indicating a position and a direction of a tool; and a three-dimensional position measuring means for measuring a position and a direction of a surgical field and also the position and the direction of said tool, wherein said position indicating means and said three-dimensional position measuring means are fixed, so that relative positional relationship therebetween is constant.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein:

FIGS. 10(a) and 10(b) are views for explaining steps for positioning the surgical tool, and in particular, wherein; FIG. 10(a) shows the condition where the laser beam is emitted to indicates a position where the surgical tool should be touched on, and FIG. 10(b) the condition where the surgical tool is touched on while fitting to the indication of the laser beam.

DETAILED DESCRIPTION OF THE INVENTION

Figure 1:
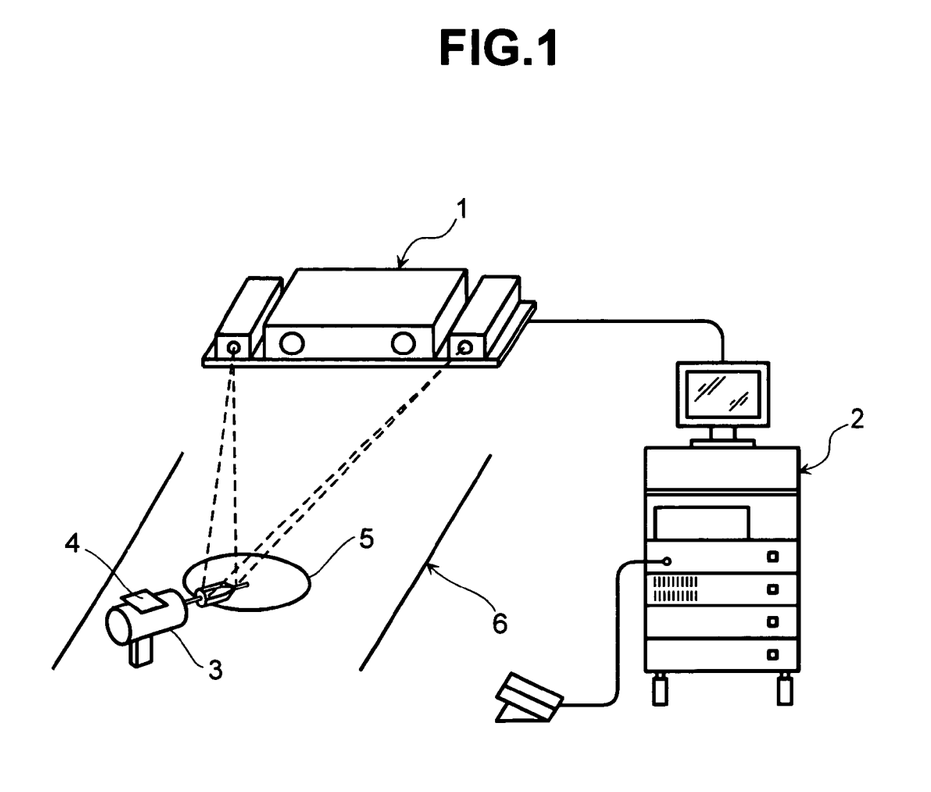
FIG. 1 is a view for showing a navigation system diagrammatically, including a position measuring apparatus therein, under the condition of being used.

Hereinafter, a position measuring apparatus, as an embodiment according to the present invention, will be fully explained by referring to the attached drawings. FIG. 1 is a view for showing the entire structure of a navigation system, diagrammatically, which applies therein the position measuring apparatus, integrating a position indicating function therein. This navigation system is constructed with a position measuring apparatus 1 and a control unit 2, mainly.

The present embodiment shows a case, where the position measuring apparatus 1 measure an infrared marker 4, which is attached onto a surgical (or operation) tool 3 to be used in the surgical operation, and guides the surgical tool 3 through emission of a laser beam in a surgical field (or an operation portion) 5, thereby conducting the surgical operation thereon. However, in the present embodiment, the position measuring apparatus is used in a spinal column alignment correcting operation; i.e., a surgical operation for correcting or remedying alignment of the backbones, through fixing them in the vertical direction, such as, by means of a plate, a rod, a screw or a wire, etc., being made of a metal, for curing the backbones, which are bent or curved, instable in the condition thereof, or collapsed.

Figure 2:
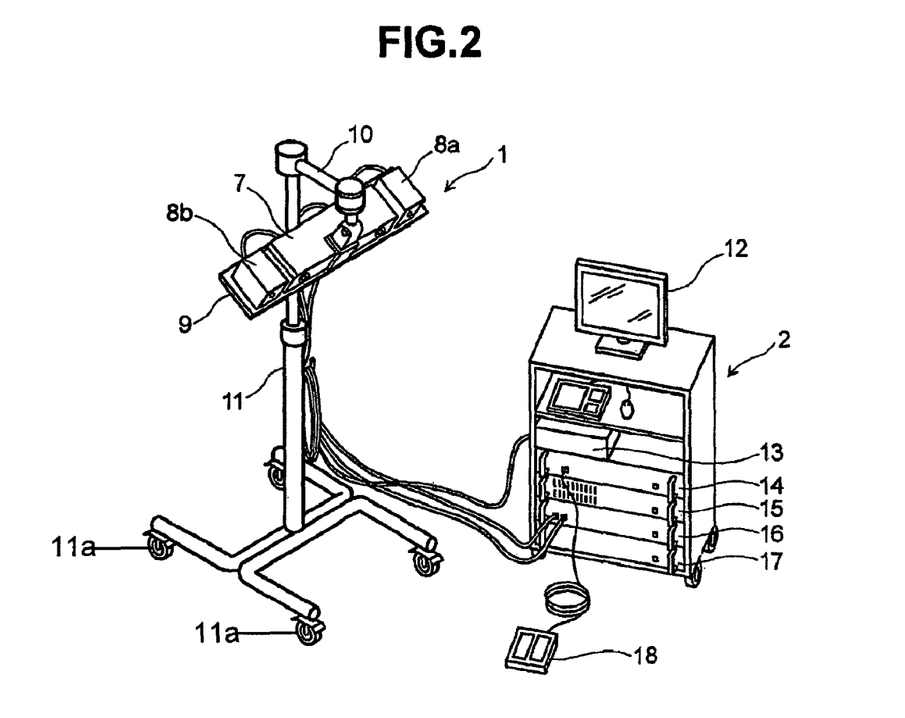
FIG. 2 is a structure view of the navigation system.

FIG. 2 is a perspective view for showing a navigation system having the position measuring apparatus 1 and the control unit 2 therein. The position measuring apparatus 1 comprises a three-dimensional (3-D) position measuring means 7, two (2) pieces of laser beam emitting means 8a and 8b, and a base 9, on which the 3-D position measuring means 7 and the laser beam emitting means 8a and 8b are fixed. This position measuring apparatus 1 is held by means a flexible arm 10, which can be fixed freely at any position and with any direction thereof, and further this flexible arm 10 is held by means of a stand 11, which can move freely with an aid of casters 11a.

With using the position measuring means constructed in this manner, it is possible to fix the 3-D position measuring means 7 and the laser beam emitting means 8a and 8b on the base 9, and thereby to move and set them at a desired position under the condition of not changing the relative positions between them. Further, the 3-D position measuring means 7 is a device or an apparatus, which measures the infrared marker 4 irradiating or reflecting an infrared (see FIG. 1) by means of a plural number of cameras, thereby measuring the 3-D position of the infrared marker 4. This 3-D position measuring means may be a position measuring means, which utilizes therein a PSD (Position Sensitive Detector), etc.

The control unit 2 controls the navigation system. The control unit 2 guides an operation of the navigation information, and it comprises a monitor 12, on which a navigation screen is displayed, and a position measuring means control unit 13 for controlling light irradiation timings of the infrared marker 4, so that the 3-D position measuring means 7 can measure the position thereof, and also the 3-D position measuring means 7. The control unit 2 further comprises an input control unit 14, to which is connected a foot switch 18, to be used by a surgeon for operating the navigation system during the surgical operation, a CPU unit 15 for executing various calculations, as a core of the navigation system, a keyboard and a mouse, being connected with the CPU unit 15, to be used in inputting of data and/or operation of the navigation system, a laser beam emitting means control unit 16 for controlling the direction of the laser beams emitted from the laser beam emitting means 8a and 8b, and an electric power unit 17 for supplying electric power to each of the units within the control unit 2.

Figure 3:
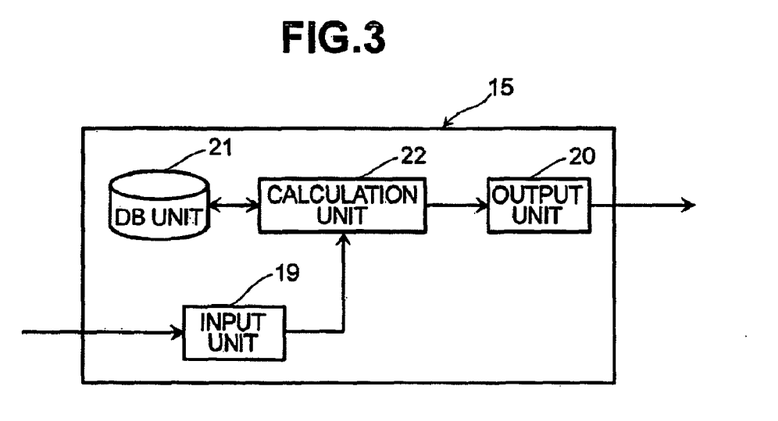
FIG. 3 is a block diagram of a CPU unit to be used in the system shown in FIG. 2 mentioned above.

The structure of the CPU unit 15, to be the core of the control unit 2, is shown in a block diagram of FIG. 3. The CPU unit 15 comprises an input unit 19 and an output unit 20, a DB (Database) unit 21, and also a calculation unit 22. The input unit 19 receives a signal inputted from the input control unit 14 and the position measuring means control unit 13, and thereby carrying a role of function of transmitting it to the calculation unit 22.

The output unit 20 carries the functions; such as, of displaying the information transmitted from the calculation unit 22 on the monitor 12, and also of transmitting it to the laser beam emitting means control unit 16, as an interface therebetween. The DB unit 21 is a memory means, being provided for holding therein, programs for achieving the functions of the CPU unit 15, information relating to a plan of the surgical operation inputted before that operation, and log information, which are all of the information inputted through the input portion during the surgical operation.

The calculation portion 22 calculates out emit angles of the laser beams, upon basis of the information inputted from position measuring means control unit 13 and the information relating to the plan of surgical operation inputted before that operation, thereby to produce the navigation information displayed on a screen, and also, it executes a calculation for producing parameters to be transmitted to the laser beam emitting means control unit 16.

Figure 5:
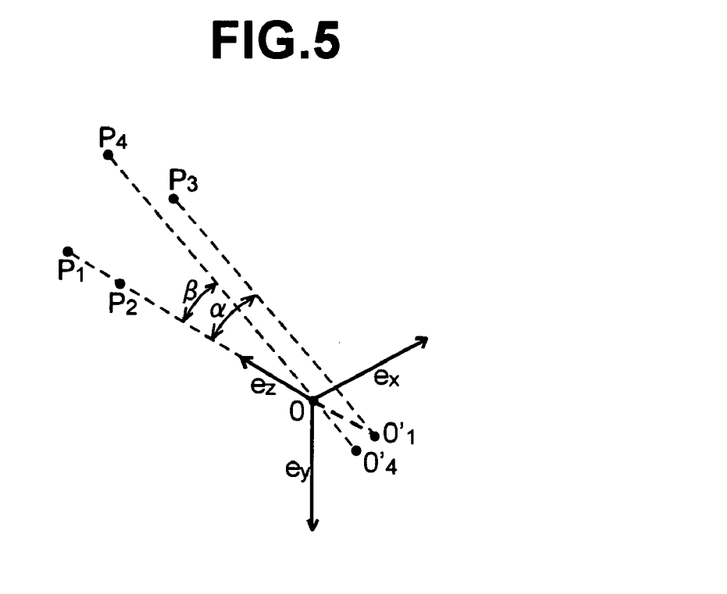
FIG. 5 is a view for explaining a calibration operation of the laser beam emitting means.

Before using the navigation system, a calibration is made on the navigation system. The details thereof will be explained below. In an operation of the calibration, correspondence is built up in emit positions and directions of the laser beams emitted from the laser beam emitting means 8a and 8b, between the coordinates defined in the navigation system.

Figure 4:
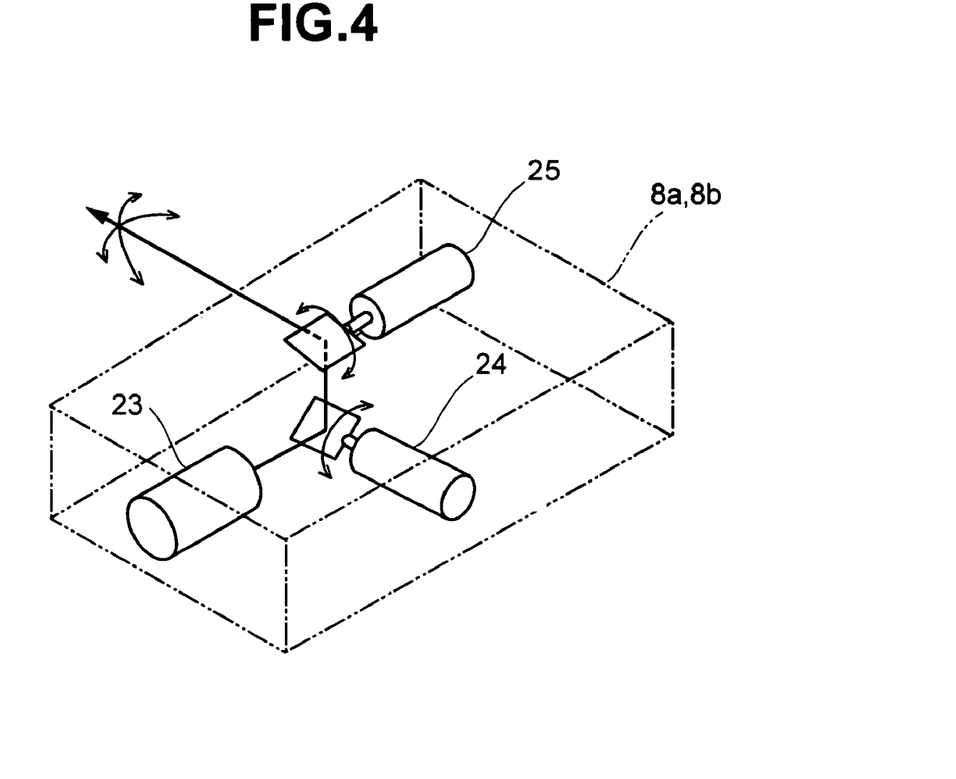
FIG. 4 is a diagrammatical view of a laser beam emitting means to be used in the system shown in FIG. 2 mentioned above.

FIG. 4 shows the interior structure of the laser beam emitting means 8a or 8b, diagrammatically. The laser beam emitting means 8a or 8b includes a laser pointer 23 for emitting the laser beam, and a galvano-scanner 24 for turning the laser beam emitted from the laser pointer 23 in the horizontal plane, and another galvano-scanner 25 for turning it in the vertical plane.

The emitting position of the laser beam is measured while changing the emit angle of the laser beam. In the present embodiment, the emit angle of the laser beams can be defined, such as, $(\alpha_{24}, \beta_{25})$ with using mirror angles, since they are equivalent to the mirror angles $\alpha_{24}$ and $\beta_{25}$ of two (2) pieces of the galvano-scanners 24 and 25. When the mirror angles of the two (2) pieces of galvano-scanners 24 and 25 are (0, 0), the emitting position of the laser beams can be expressed by $P_1$ and $P_2$. And it is assumed that the emitting position of the laser beam is $P_3$ when the mirror angles are $(\alpha, 0)$, and that the emitting position thereof is $P_4$ when the mirror angles $(0, \beta)$. The coordinates of those emitting positions $P_1$ to $P_4$ are measured. The mirror angles $\alpha$ and $\beta$ may be arbitrary angles, but excepting for being zero (0) degree. However, it is preferable to use the maximum swing angles of the mirror angles of the galvano-scanners. The coordinates of the emitting positions $P_1$ to $P_4$ are measured by using the 3-D position measuring means 7.

From a relationship obtained between the angles of the galvano-scanners and the emitting positions, the setting positions and directions of the laser beam emitting means 8a and 8b are calculated out. Herein, it is assumed that a central position of the mirror of the galvano-scanner 25 is "O". And, it is also assumed that a unit vector of the laser beam is "$e_z$" in an emit direction thereof when both the mirror angles of the two (2) pieces of galvano-scanners are zero (0), that a unit vector is "$e_x$" in a direction of changing the emitting direction of the laser beam when only the galvano-scanner 24 is rotated around, and that a unit vector is "$e_y$" in a direction of changing the emitting direction of the laser beam when only the galvano-scanner 25 is rotated around. Also, it is assumed that a distance between those mirrors of the two (2) pieces of galvano-scanners 24 and 25 is "r", being already known. Further, it is assumed that an equivalent emitting position of the laser beam is "$O_1$'" when the mirror angle of the galvano-scanners 25 is zero (0), and that the equivalent emitting position is "$O_4$'" when the mirror angle is $\beta$.

The unit vector $e_z$ can be obtained from the emitting positions $P_1$ and $P_2$ through the following equation:

$$e_z = \frac{\overrightarrow{P_2 P_1}}{\overline{P_2 P_1}}$$

A perpendicular line is obtained, which is drawn from the emitting position $P_3$ towards a line, which is defined by the emitting position $P_1$ and the unit vector $e_z$, and if assuming that a foot of the perpendicular can be expressed by $P_3'$, then the unit vector $e_x$ can be obtained from the following equation:

$$e_x = \frac{\overrightarrow{P_3'P_3}}{P_3'P_3}.$$

A perpendicular line is obtained, which is drawn from the emitting position $P_4$ towards the line, which is defined by the emitting position $P_1$ and the unit vector $e_z$, and if assuming that a foot of the perpendicular can be expressed by $P_4'$, then the unit vector $e_y$ can be obtained from the following equation:

$$e_y = \frac{\overrightarrow{P_4'P_4}}{P_4'P_4}$$

Since an angle $\angle P_4'OP = \beta$ the line segment $P_4'OP$ can be expressed by the following equation:

$$P_4'OP_4 = \frac{P_4'P_4}{\tan\beta}$$

Accordingly, the central position "O" of the mirror can be obtained from the following equation:

$$O = P_4' - P_4'O \cdot e_z$$

From the above, the central position "O" of the mirror of the galvano-scanner 25, being equivalent in the setting potion of the laser emitting means 8a or 8b, and the unit vectors $e_x$, $e_y$ and $e_z$ can be obtained, each being equivalent to the setting direction thereof. Further, if the emitting position of the laser beam can be measured with the emitting angles at least of three (3) pieces thereof, it is possible to obtain the setting position and the direction of the laser beam emitting means 8a or 8b.

Figure 6:
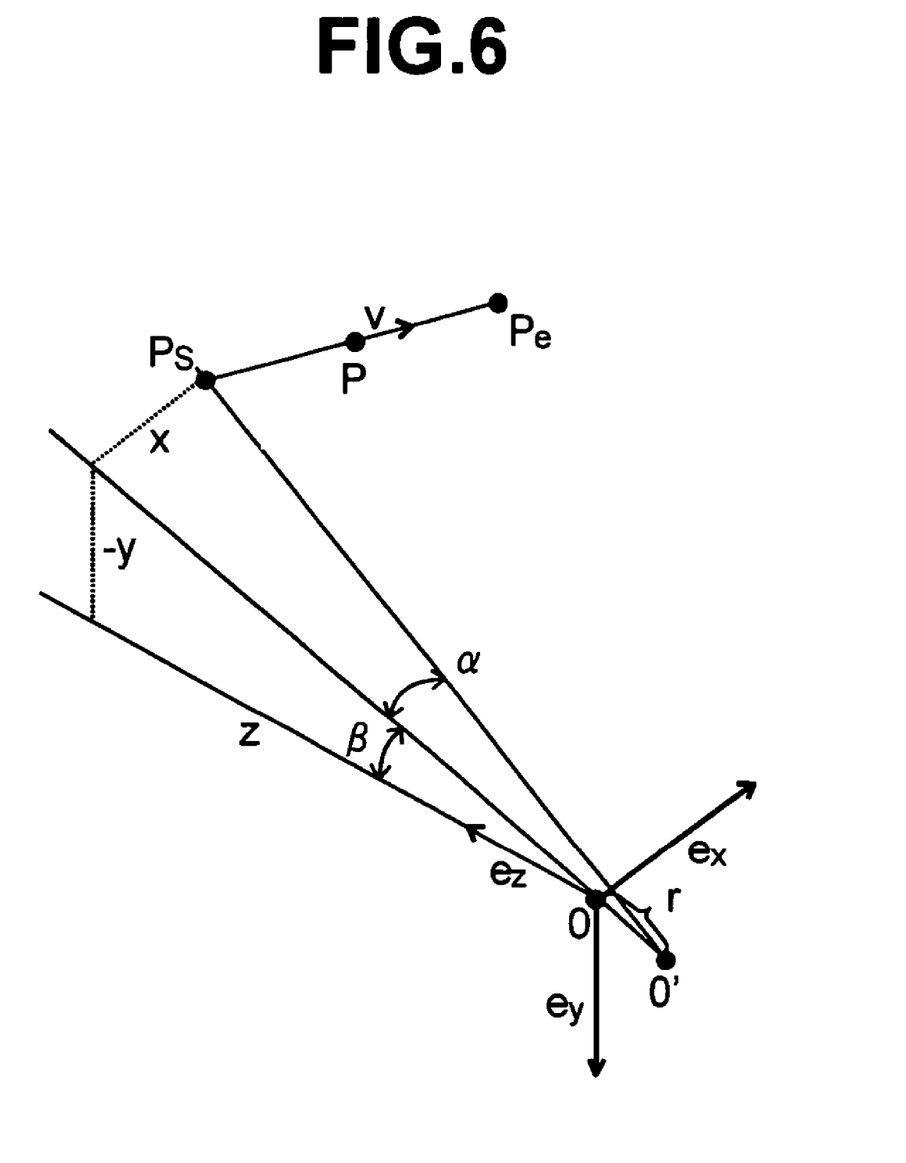
FIG. 6 is a view for explaining a method for obtaining an instruction emit angle of the laser beam.

Explanation will be given on an example of calculation processing, in particular, for obtaining an instruction emit angle of the laser beam from a target position and direction of the surgical tool and the setting position and direction of the laser beam emitting means 8a or 8b, by referring to FIG. 6. This FIG. 6 shows the laser beam emitting means 8a or 8b, which is shown in FIG. 4 mentioned above.

It is assumed that the target position of the surgical tool is "P", and that a unit vector indicative of a target direction is "v". For indicating the position and the direction of the surgical tool, it is sufficient that the laser beam is emitted onto a line segment $P_sP_e$ including the target position therein, on a straight line which can be defined by those target position "P" and the unit vector "v". The mirror angles $\alpha_s$, $\beta_s$ and $\alpha_e$, $\beta_e$ of two (2) pieces of the galvano-scanners can be obtained when the laser beam is emitted on a start point $P_s$ of the line segment $P_sP_e$ and an end point $P_e$ thereof, respectively. Within the region between those mirror angles; e.g., $(\alpha_s, \beta_s)$ $(\alpha_e, \beta_e)$, the mirror angles of those two (2) pieces of galvano-scanners are changed in synchronism with each other.

The mirror angles $\alpha$ and $\beta$ of the galvano-scanners 24 and 25, bringing the laser beam to emit upon the start point $P_s$ of the line segment $P_sP_e$, can be obtained as below, by using the setting position "O" and the setting direction $e_x$, $e_y$, and $e_z$ of the laser beam emitting means 8a or 8b. Thus, (x, y, z) is obtained, which satisfies the following equation:

$$\overrightarrow{OP_s} = x \cdot e_x + y \cdot e_y + z \cdot e_z = (e_x \ e_y \ e_z)\begin{pmatrix}x\\y\\z\end{pmatrix}$$

$$\begin{pmatrix}x\\y\\z\end{pmatrix} = (e_x \ e_y \ e_z)^{-1}\overrightarrow{OP_s}$$

From the (x, y, z) obtained, the mirror angels $\alpha$ and $\beta$ can be expressed by the following equation:

$$\alpha = \tan^{-1}\frac{x}{\sqrt{y^2 + z^2} + r}$$

$$\beta = \tan^{-1}\frac{-y}{z}$$

In the similar manner, the mirror angles of the galvano-scanners can be obtained, for bringing the laser beam to emit upon the end point of the line segment $P_sP_e$.

According to the present embodiment, reference values to the galvano-scanners can be obtained, being equivalent to the reference emitting angle of the laser beam, from the target position and the direction (i.e., orientation) of the surgical tool, and also the setting positions and the directions of the laser beam emitting means 8a and 8b. Further, in the position indicating system for indicating the position and the direction of the tool, it is possible to make such a control, that an intersection line formed by laser beam planes, which are emitted in a plane-like manner from the laser beam emitting means, is coincident with a straight line, which is defined by the target position and the direction of the tool, if having at least two (2) pieces of the laser beam emitting means, each being able to control the emit angle of the laser beam, and a control means for controlling the laser beam emitting means, as well. With this, it is possible to provide or indicate the target position visually for the surgeon.

In a case when moving the position measuring apparatus 1 supported on a stand 11, the relative position among the laser beam emitting means 8a and 8b and the 3-D position measuring means 7 does not change. In this case, the calibration operation is not necessary to be done among the laser beam emitting means 8a and 8b and the 3-D position measuring means 7 one another. Though the coordinate system of the position measuring apparatus 1 swerves away from surgical field, however since the 3-D position measuring means 7 always measures the position and the direction of the infrared marker attached on the surgical field, at a predetermined time period, and therefore a fitting operation is executed between the coordinates of the surgical field and the position measuring apparatus 1. Namely, the CPU unit 15 in the control unit 2 calculates out the position of the surgical field from the position and the direction of the infrared marker. Accordingly, the surgeon can move the position measuring apparatus 1 to a desired position, freely, without consciousness.

Since the relative position among the laser beam emitting means 8a and 8b and the 3-D position measuring means 7 does not change, even when the position measuring apparatus 1 is moved during the operation of, such as, the surgical operation, etc., therefore it is enough to conduct the calibration operation mentioned above, but only when the position measuring apparatus is delivered to and/or when conducting a periodic inspection, for example. Thus, the calibration should not be conducted every time when conducting the surgical operation or moving the position measuring apparatus 1, therefore the position measuring apparatus comes can be treated easily.

Figure 7:
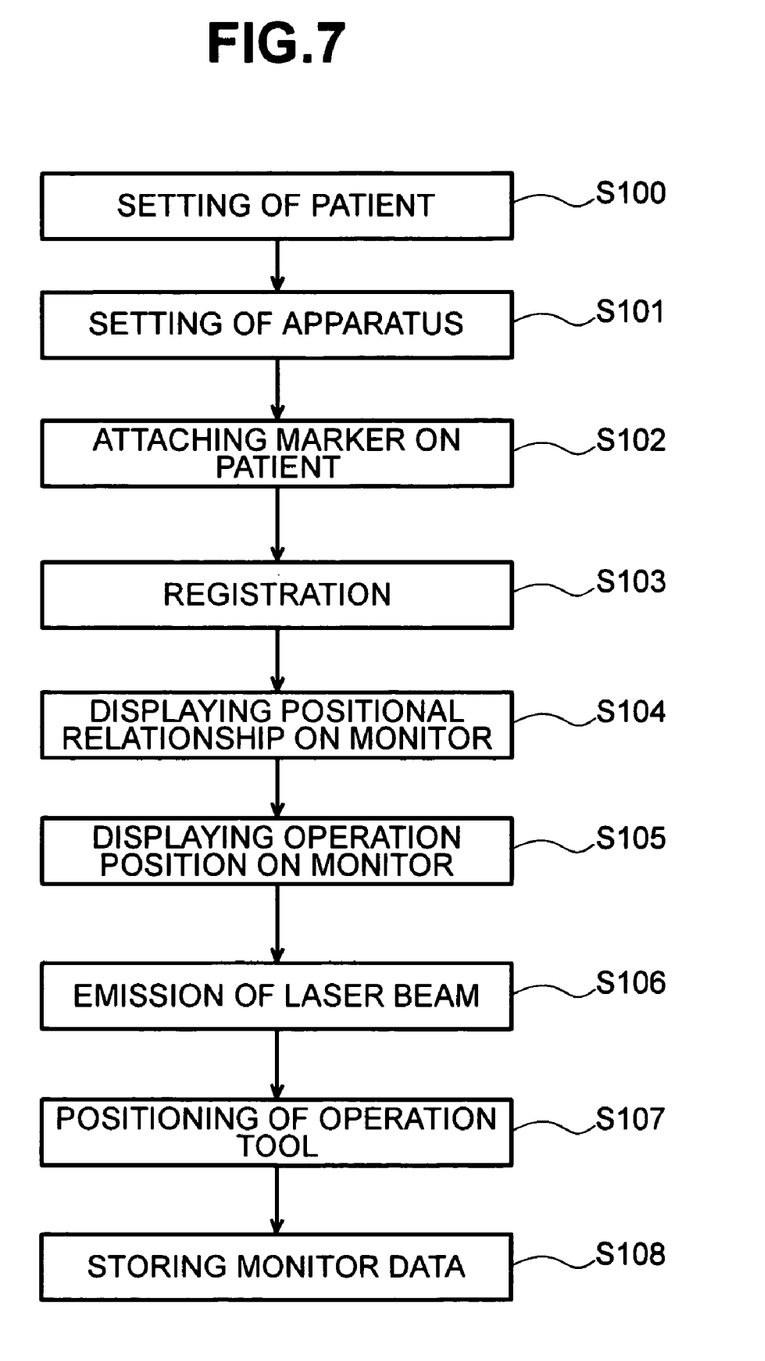
FIG. 7 is a flowchart for showing steps of using the navigation system.

After completion of the calibration operation, the surgeon starts the processes of the surgical operation. The processes of using the navigation system for use in the surgical operation are shown in FIG. 7. The surgeon has already taken the 3-D data of the backbones of a patient who will have the operation, in advance, before performing an orthodontic operation for the backbone alignment, for example, by means of, such as, a MRI (Magnetic Resonance Imaging) and/or a CT (Computed Tomography) scanner, etc. And then, a plan of surgical operation is made out upon the basis of the taken 3-D data of the backbones, and it is decided at which position should be touched the surgical tool on the patient. Those data are inputted into the control unit 2, in advance.

The surgeon carries the patient who will have the surgical operation on a surgical bed, thereby fixing her/his thereon, and makes setting to the patient before the surgical operation (S100). And the surgeon moves the position measuring apparatus 1 to an appropriate position, thereby conducting setting of the measuring apparatus 1 (S101). The infrared marker is attached to the backbones of the patient, on which the surgical operation will be done, and thereby enabling to identify or confirm the position of the backbones of the patient with using the 3-D position measuring means 7 (S102).

Figure 8:
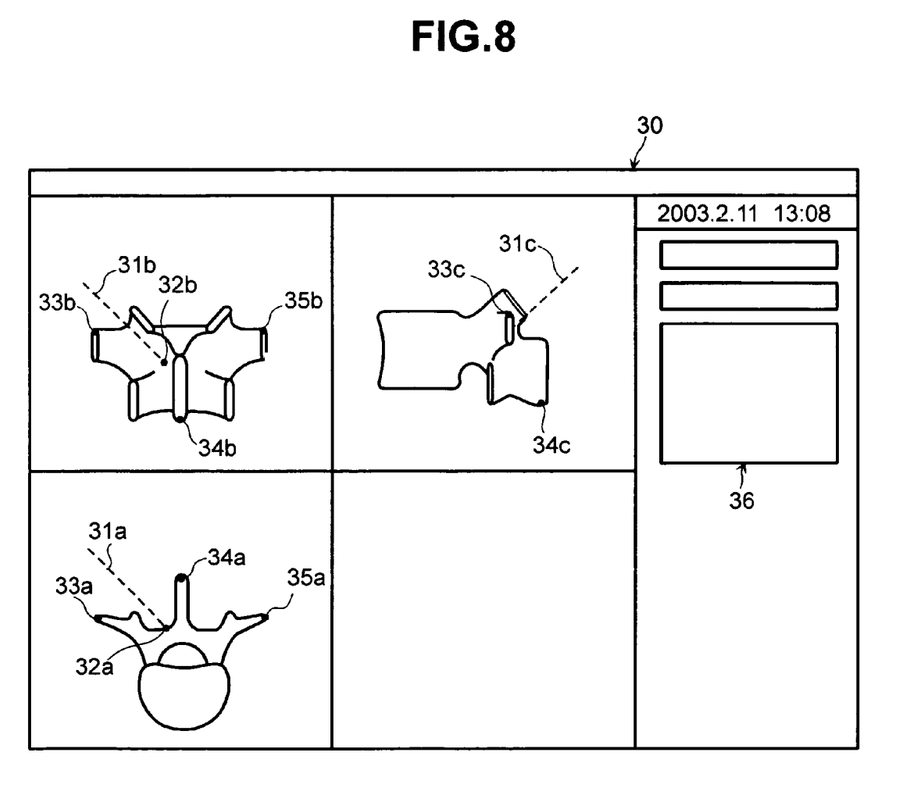
FIG. 8 is a view of an example of a display screen after completion of a registration operation in the navigator system.

Then, a registration operation is conducted (S103), for the purpose of coordinating or adjusting between the position information obtained through detection of the infrared-marker attached on the backbones and a model based on the 3-D data of the backbones (hereinafter, being called by a "backbone model"), as a surgical field of the patient, which was taken in advance by means of the CT scanner and/or the MRI, etc. Upon basis of the information obtained through that registration operation, the CPU unit 15 fits the backbone model to the position of the backbone of the patient, which is measured actually. Then, the CPU unit produces the navigation screen indicating the positional relationships thereof, and displays it on the monitor 12 (S104). The CPU unit 15 displays a surgical field on the navigation screen displayed on the monitor, upon basis of the information of the surgical operation plan, which was already inputted in advance (S105). FIG. 8 shows an example of the navigation screen of the surgical field displayed on the monitor 12.

The navigation screen 30 displays three (3) views thereon; i.e., a front view, a top view and a side view of the backbone model, as the surgical field. An operating portion 36 for operating the navigation screen is displayed on the right-hand side of the screen. In FIG. 8, position measurement points 33a-33c, 34a-34c, and 35a-35c on the backbones are displayed overlapping with each other, which are used in the registration operation mentioned above. Those having the same reference numerals, but being attached with different suffixes, indicate the views of the same position measurement points seeing from different angles, and those having different reference numerals indicate the different position measurement points, respectively. A point 32a is the position where the surgical tool should be touched on according to the plan. A broken line 31a is an auxiliary line for indicating the direction of touching of the surgical tool according to the plan.

Figure 9:
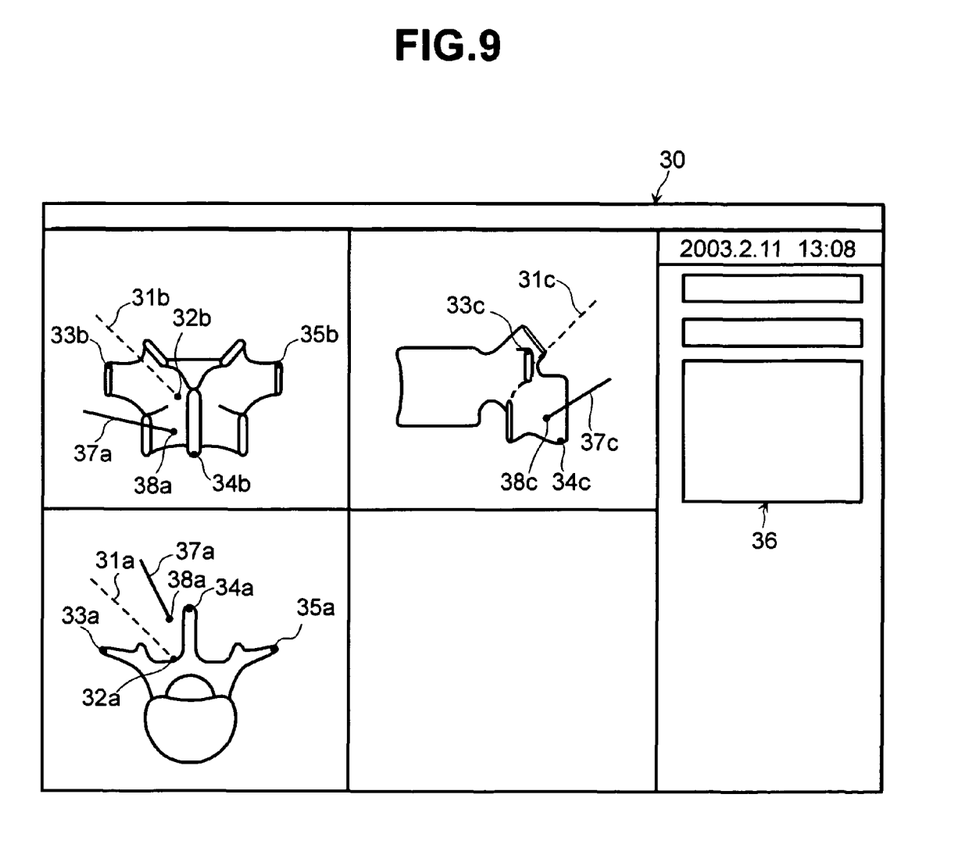
FIG. 9 is a view of an example of the display screen where a tip and a direction of a surgical tool are displayed on the navigation system.

The surgeon moves the surgical tool up to the vicinity of the surgical field of the patient. In this instance, on the navigation screen on the monitor 12 is displayed the tip of the surgical tool with the position and the direction thereof, which are detected through the infrared marker attached on the surgical tool by means of the 3-D position measuring means 7 (see FIG. 8). FIG. 9 is another navigation screen 30', and in this FIG. 9, further solid lines 38a and 37a are displayed overlapping on the three (3) views of the backbone model on the navigation screen 30 shown in FIG. 8 mentioned above, indicating the position 38a of the tip of the surgical tool and the direction of the surgical tool. From this screen shown in FIG. 9, the surgeon can confirm the position of the surgical tool, easily, only by confirming it on the monitor.

The CPU unit 15 transmits emitting parameters of the laser beams to the laser beam emitting means control unit 16. Then, the laser beams are emitted in the plane-like manner from the laser beam emitting means 8a and 8b located at two (2) spots (S106). An intersection line is formed with the laser beams emitted in the plane-like manner from the laser beam emitting means 8a and 8b located at two (2) spots, and this intersection line coincides with the broken line 31a, which is displayed on the navigation screen 30 to be the direction of touching the surgical tool according to the plan. An intersection point formed with two (2) lines drawn by two (2) laser beams on the surgical field coincides with the position 32a where the surgical tool should be touched according to the plan.

The surgeon actually conducts positioning of the surgical tool (S107). A method for positioning of the surgical tool will be explained by referring a diagrammatic view shown in FIGS. 10(a) and 10(b). Herein is shown an example where a hand drill is used as the surgical tool. On an internal portion of teeth of the hand drill 3 is attached a white-colored sleeve 40 for use of the positioning thereof, for the purpose of easy distinguish of the laser beam. On the sleeve 40, there are drawn lines 41 in a several number thereof, in parallel to a rotation axis of the hand drill 3.

Figure 10A:
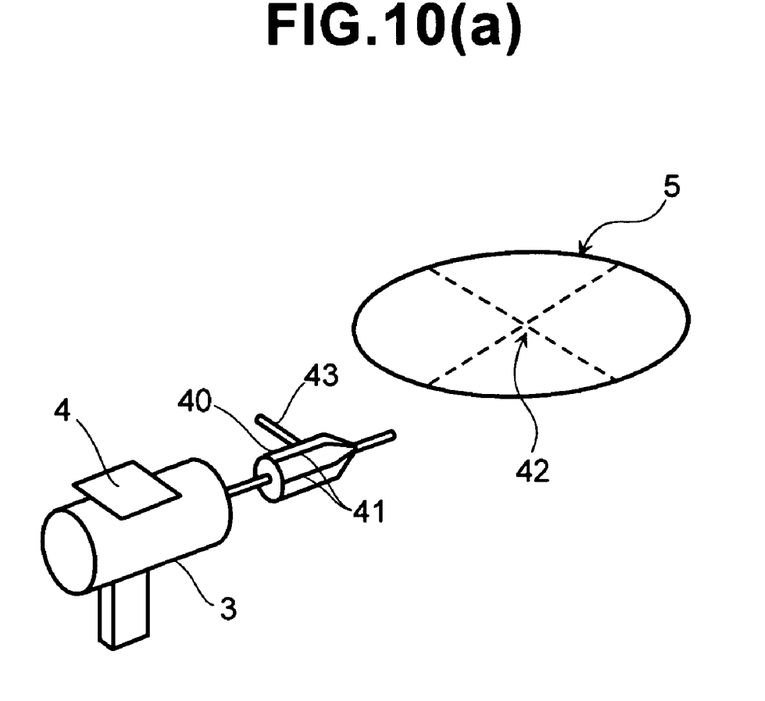

FIG. 10(a) shows a stage just before using the hand drill 3. Namely, it is the condition where the laser beams are emitted from, thereby indicating the position where the hand drill 3 should be touched on. In this stage, on the surgical field 5 of the patient is projected an intersection 42, which is formed through crossing of the laser beams emitted in the plane-like manner from the laser beam emitting means 8a and 8b. That intersection point 42 is the position where the drill 3 should be actually touched thereon. The surgeon brings the hand drill 3 to be touched on the intersection point at the tip thereof while holding a grip of the hand drill 3 and a grip rod 43, which is attached on the sleeve 40 provisionally.

Figure 10B:
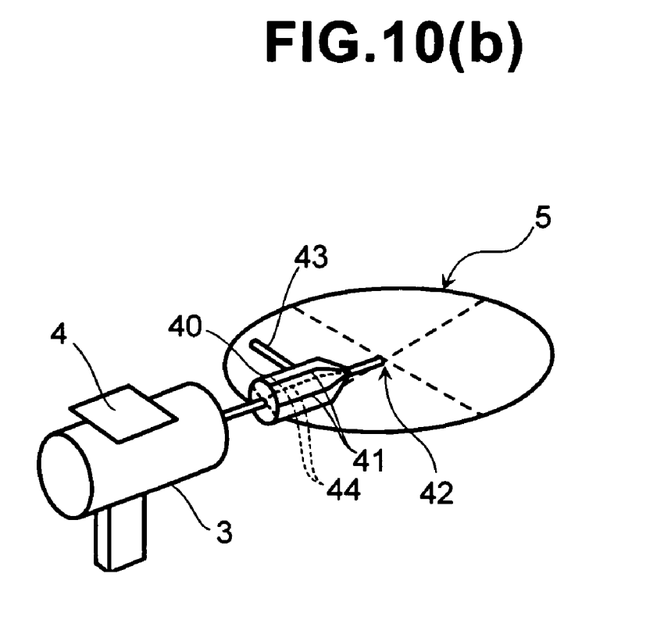

FIG. 10(b) shows the condition where the hand drill 3 is touched on an indicating point by the laser beams. When fitting the tip of the hand drill 3 and the intersection point 42 at the position thereof, a locus or track 44 of the two (2) pieces of laser beams is projected on the sleeve 40 of the hand drill 3, by means of the laser beams emitted in the plane-like manner from the laser beam emitting means 8a and 8b. The surgeon determines the direction of the hand drill 3, so that the track 44 of the two (2) pieces of laser beams comes to be in parallel with the lines 41, which are drawn on the sleeve in parallel with the rotation axis of the hand drill 3. With such the steps as was mentioned above, it is possible to fit the hand drill 3 as the surgical tool to the potion and direction of the target. And, it is also possible for the surgeon to perform the surgical operation, while confirming the surgical tool touched on the surgical field and also the actual surgical field, visually, with her/his eyes, but without seeing them on the monitor 12.

The surgeon precedes the surgical operation in accordance with the surgical operation plan, which was inputted in advance. In that instance, she/he changes over the navigation screen by pushing down the foot switch 18 on foot. All of the monitor data, such as, the position information measured during a series of surgical operations, etc., are stored in the DB portion of the CPU unit 15 (S108). However, in a case when the laser beams emitted from the laser beam emitting means 8*a* and 8*b* are obstructed or cut off by the surgical field of the patient and/or the surgical tools, etc., and also when it disturbs the surgeon, the position measuring apparatus 1 is moved to a desired position and is set there.

According to the present embodiment, if the position measuring apparatus is moved in the position, accidentally, no calibration operation is necessary; therefore the surgical operation can be performed continuously. Also, since the target position and the moving direction of the surgical tool are indicated with using the laser beam emitting means, therefore the surgeon can concentrate her/his attention onto the surgical operation at hand, without watching the navigation screen, thereby enabling to prevent the surgical tool from shifting in the position thereof. Accordingly, it is possible to lighten a load upon the surgeon, during the surgical operation.

In the embodiment mentioned above, though the position measuring apparatus is constructed with the movable type stand and the movable type of control unit, etc., however it is also possible to hold the position measuring apparatus by means of a flexible arms or the like, which is fixed onto a ceiling, or to install the position measuring apparatus together with the laser beam emitting means and the 3-D position measuring means into the same housing. Also, though the position measuring apparatus is used in the surgical operation in the present embodiment mentioned above, however it may be applied into various fields, such as, civil engineering works, manufacturing processes of industrial products, etc., other than the surgical operation.

According to the present embodiment mentioned above, since the relative positional relationship between the position indicating apparatus and the position measuring means is constant or unchanging even if moving the position measuring apparatus during the surgical operation, therefore no calibration operation is necessary, and the position measuring apparatus can be moved to a desired position, freely. Accordingly, it is possible to assist the surgical operation, in particular, in a case when applying the position measuring apparatus into the surgical operation.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraces therein.

What is claimed is:

1. A position measuring apparatus for surgery comprising:
   a position indicating means for indicating two axial setting position and two plane setting direction of a surgical tool, said position indicating means including a pair of laser beam emitting means for emitting two respective laser beams scanned to form two planes, respectively, that intersect in a surgical field, where said two-axial setting-position is indicated by an intersection of said laser beams on a surface of a surgical object;
   three dimensional position measuring means for measuring a position and a direction of said surgical field and also the setting-position and the setting-direction of said surgical tool; and
   a control unit for controlling operation of said position indicating means and said three-dimensional position measuring means,
   wherein said position indicating means and said three-dimensional position measuring means being fixed on a common base, so that relative positional relationship therebetween is constant; and
   wherein said setting-direction for said surgical tool is given in a form of an intersection line formed by an intersecting said two planes which are formed by said two respective laser beams.

2. A position measuring apparatus, as described in the claim 1, wherein said position measuring apparatus is held on a stand, which is changeable in its position and direction by being movable while keeping the relative positional relationship between said position indicating means and said three-dimensional position measuring means.

3. A position measuring apparatus, as described in the claim 1, wherein said position measuring apparatus is held by an arm, the arm extending from a ceiling and being changeable in a position and a direction by being movable while keeping the relative positional relationship between said position indicating means and said three-dimensional position measuring means.

4. A position measuring apparatus, as described in the claim 1, wherein said position measuring apparatus is used for indicating a position and a direction of said surgical tool during a surgical operation.

5. A position measuring apparatus, as described in the claim 1, wherein said surgical tool including plural line indicia marked thereon, serving as reference lines for parallelly-aligning scanning lines of said laser beams impinging onto said surgical tool to parallelly-align with said line indicia, as a guide to effect said setting-direction of said surgical tool.

6. A position measuring apparatus for surgery comprising:
   a position indicating means for guiding two axial setting position and a setting-orientation of a surgical tool, said position indicating means including a pair of laser beam emitting means for emitting respective laser beams that intersect in a surgical field, where said two-axial setting-position is indicated by an intersection of said laser beams on a surface of a surgical object;
   three dimensional position measuring means for measuring a position and an orientation of said surgical field and also the setting-position and the setting-orientation of said surgical tool; and
   a control unit for controlling operation of said position indicating means and said three-dimensional position measuring means,
   wherein said position indicating means and said three-dimensional position measuring means being fixed on a common base, so that relative positional relationship therebetween is constant; and
   wherein said setting-orientation for said surgical tool is given in a form of an intersection line formed by an intersecting said two planes which are formed by said two respective laser beams.

7. A position measuring apparatus, as described in the claim 6, wherein said position measuring apparatus is held on a stand, which is changeable in its position and orientation by being movable while keeping the relative positional relationship between said position indicating means and said three-dimensional position measuring means.

8. A position measuring apparatus, as, described in the claim 6, wherein said position measuring apparatus is held by an arm, the arm extending from a ceiling and being changeable in a position and an orientation by being movable while keeping the relative positional relationship between said position indicating means and said three-dimensional position measuring means.

9. A position measuring apparatus, as described in the claim 6, wherein said position measuring apparatus is used for indicating a position and an orientation of said surgical tool during a surgical operation.

10. A position measuring apparatus, as described in the claim 6, wherein said surgical tool including plural line indicia marked thereon serving as reference lines for parallelly-aligning scanning lines of said laser beams impinging onto said surgical tool to parallely-align with said line indicia as a guide to effect said setting-orientation of said surgical tool.

11. A position measuring-apparatus for surgery comprising:
- a position indicating means for guiding two axial intersection point as a setting position and two plane intersection line as a setting-orientation of a surgical tool, said position indicating means including a pair of laser beam emitting means for emitting two respective laser beams scanned to form two planes that intersect in a surgical field, where said two-axial intersection point is indicated by an intersection of said laser beams on a surface of a surgical object;
- three dimensional position measuring means for measuring a position and an orientation of said surgical field and also the setting-position and the setting-orientation of said surgical tool; and
- a control unit for controlling operation of said position indicating means and said three-dimensional position measuring means,
- wherein said position indicating means and said three-dimensional position measuring means being fixed on a common base, so that relative positional relationship therebetween is constant, and
- wherein said two-plane intersecting line is given by an intersecting said two planes which are formed by said two respective laser beams.

12. A position measuring apparatus, as described in the claim 11, wherein said position measuring apparatus is held on a stand, which is changeable in its position and orientation by being movable while keeping the relative positional relationship between said position indicating means and said three-dimensional position measuring means.

13. A position measuring apparatus, as described in the claim 11, wherein said position measuring apparatus is held by an arm, the arm extending from a ceiling and being changeable in a position and an orientation by being movable while keeping the relative positional relationship between said position indicating means and said three-dimensional position measuring means.

14. A position measuring apparatus, as described in the claim 11, wherein said surgical tool including plural line indicia marked thereon, serving as reference lines for parallelly-aligning scanning lines of said laser beams impinging onto said surgical tool to parallelly-align with said line indicia, as a guide to effect said setting-orientation of said surgical tool.

* * * * *